United States Patent
Conwell et al.

(10) Patent No.: US 7,668,288 B2
(45) Date of Patent: Feb. 23, 2010

(54) DISCRETE SAMPLING OF GAMMA RAY FIELD OVER MULTIPLE PORTIONS USING MULTIPLE HEADS WITH SPACES BETWEEN THE DIFFERENT PORTIONS

(75) Inventors: Richard L. Conwell, Del Mar, CA (US); Chuanyong Bai, Poway, CA (US)

(73) Assignee: Digirad Corporation, Poway, CA (US)

( * ) Notice: Subject to any disclaimer, the term of this patent is extended or adjusted under 35 U.S.C. 154(b) by 90 days.

(21) Appl. No.: 11/505,233

(22) Filed: Aug. 15, 2006

(65) Prior Publication Data
US 2007/0098132 A1 May 3, 2007

Related U.S. Application Data

(60) Provisional application No. 60/708,752, filed on Aug. 15, 2005.

(51) Int. Cl.
*G01N 23/00* (2006.01)
(52) U.S. Cl. ............................................. 378/16; 378/8
(58) Field of Classification Search ................ 378/4–20
See application file for complete search history.

(56) References Cited

U.S. PATENT DOCUMENTS

| 6,194,726 B1 | 2/2001 | Pi et al. |
| 6,639,965 B1 * | 10/2003 | Hsieh et al. ..................... 378/8 |
| 6,865,248 B1 * | 3/2005 | Rasche et al. .................. 378/8 |
| 7,164,130 B2 | 1/2007 | Welsh et al. |
| 2004/0240604 A1 * | 12/2004 | Wang et al. ................... 378/19 |
| 2005/0189494 A1 | 9/2005 | Conwell |
| 2006/0157653 A1 | 7/2006 | Conwell |
| 2006/0173302 A1 | 8/2006 | Conwell |

OTHER PUBLICATIONS

Pan, et al.; π-Scheme Short-Scan SPECT and Image Reconstruction with Nonuniform Attenuation; Feb. 1, 2003; IEEE Transactions on Nuclear Science, vol. 50, No. 1, pp. 87-96.

* cited by examiner

*Primary Examiner*—Hoon Song
(74) *Attorney, Agent, or Firm*—Law Ofc SC Harris

(57) ABSTRACT

A medical imaging system, e.g., a computed tomography system includes at least one radiation detector that is relatively rotatable with respect to an object of interest. The angular range is divided into discrete continuous acquisition ranges and unsampled angular ranges, wherein the discrete continuous acquisition ranges are separated by unsampled angular ranges.

18 Claims, 5 Drawing Sheets

DISCRETE SAMPLING OF GAMMA RAY FIELD OVER MULTIPLE PORTIONS USING MULTIPLE HEADS WITH SPACES BETWEEN THE DIFFERENT PORTIONS

CROSS-REFERENCE TO RELATED APPLICATIONS

This application claims priority to U.S. Provisional Application Ser. No. 60/708,752, filed on Aug. 15, 2005. The disclosure of the prior application is considered part of (and is incorporated by reference in) the disclosure of this application.

BACKGROUND

In general, medical imaging systems, such as computed tomography systems, comprise at least one radiation detector that detects radiation from a source, e.g., the patient. One of the patient and/or the source are rotated around an object to be examined, e.g. a patient, within an angular range.

The angular range extends from the start angle of the system to the end angle of the system. To reduce artifacts in reconstructed images, the angular range is desirably at least 180° for parallel-beam geometry, or 180° plus the fan-angle for fan-beam geometry to satisfy the data completeness condition.

If an acquisition range is less than the angular range of the system, i.e. a limited-angle acquisition range, then the object will have unsampled angular regions and consequently, the reconstructed images may have reconstruction artifacts.

SUMMARY

In one aspect of the present disclosure, a medical imaging system, e.g., a computed tomography system, includes a radiation detector, wherein the radiation detector is relatively rotatable with respect to a subject to be examined within an angular range. The angular range is divided into multiple discrete continuous acquisition ranges separated by unsampled angular ranges.

This and other aspects can include one or more of the following features:

the relative rotation of the detector may have a minimum angular step size;

the computed tomography system may have multiple radiation emitters and/or detectors;

the application of the computed tomography system may produce unsampled angular ranges that are unequal in size; and the computed tomography system may incorporate practical features, such as patient supports, motion trackers or motion correctors.

In another aspect of the present disclosure, an angularly discrete acquisition technique includes measuring a first discrete continuous acquisition range within an angular range and measuring a second discrete continuous acquisition range. Both the first discrete continuous acquisition range and the second discrete continuous acquisition range are within the angular range and are separated by an unsampled angular range.

The operation may include one or more of the following operations:

decreasing the size of the unsampled angular range;

increasing the number of unsampled angular ranges; and excluding an angular range, wherein a subject moves from a first position to a second position and then back to the first position in a short period of time.

In yet another aspect of the present disclosure, a computer program, which may be loaded into the working memory of a computed tomography system, performs an angularly discrete acquisition that measures a first discrete continuous acquisition range and measures a second discrete continuous acquisition range. Both the first discrete continuous acquisition range and the second discrete continuous acquisition range are within the angular range and are separated by an unsampled angular range.

This and other aspects can include one or more of the following functions:

the computer program may decrease the size of the unsampled angular range;

the computer program may increase the number of unsampled angular ranges; and the computer program may exclude an angular range, wherein a subject moves from a first position to a second position and then back to the first position in a short period of time.

DETAILED DESCRIPTION

The general structure and techniques, and more specific embodiments which can be used to affect different ways of carrying out the more general goals, are described herein.

The present disclosure describes a medical imaging system, e.g. a computed tomography system 1, for imaging a subject 5. Computed tomography system 1 may be, but is not limited to, a computed axial tomography (CAT) system, a single photon emission tomography (SPECT) system or a positron emission tomography (PET) system. The embodiment is capable of discontinuous data acquisition in an angular range 10.

Figure 1:
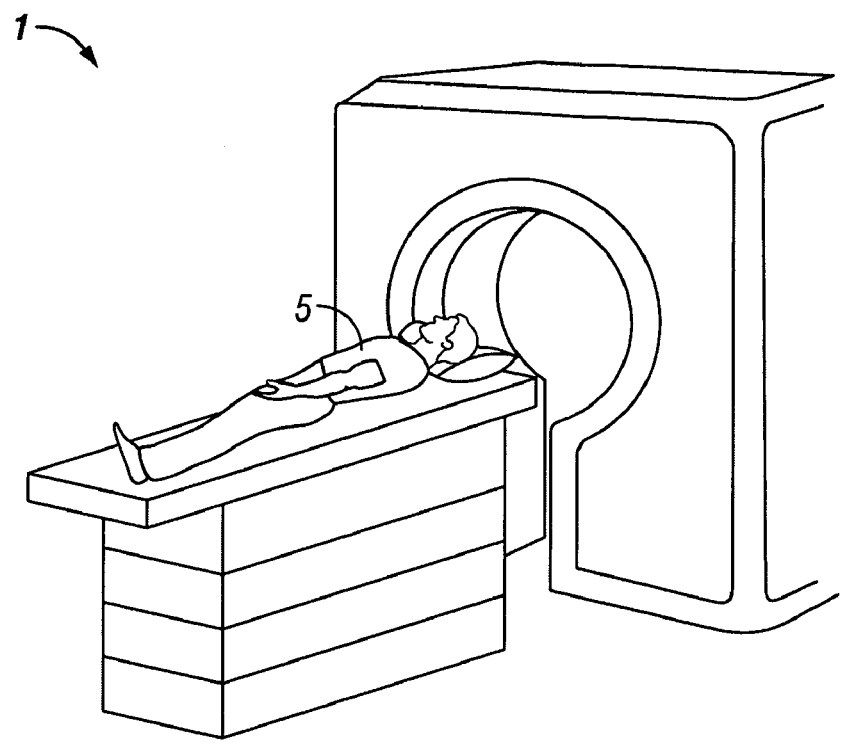
FIG. 1 illustrates an implementation of a computed tomography system.
Figure 2:
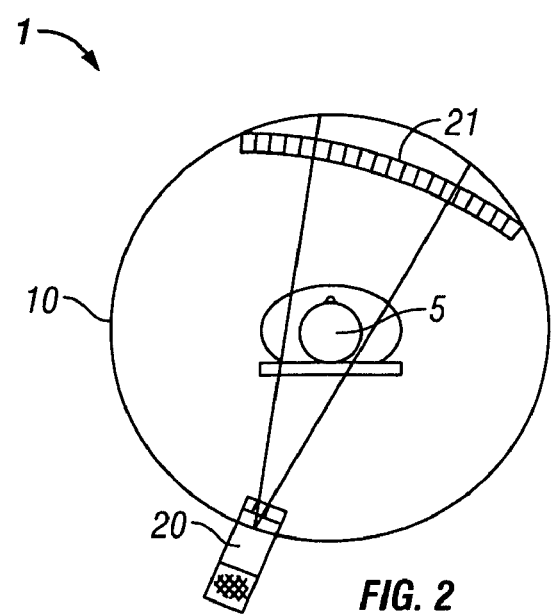
FIG. 2 illustrates an implementation of a conventional computed tomography system.
Figure 3:
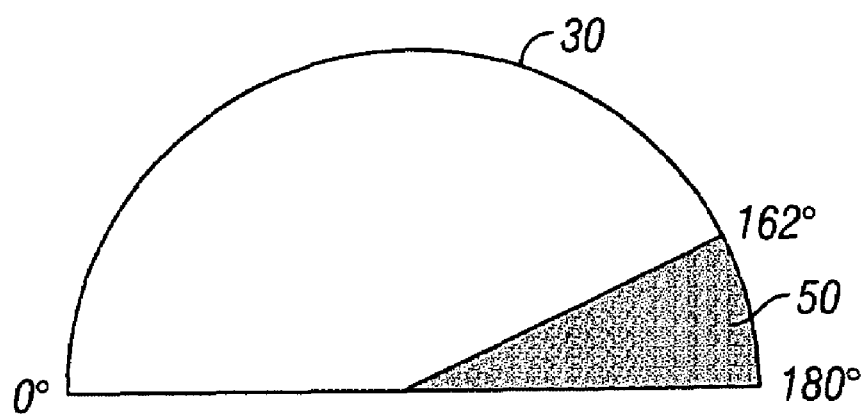
FIG. 3 illustrates the implementation of FIG. 2 with a limited angular acquisition range.

FIG. 2 illustrates a beam configuration for computed tomography system 1 having a radiation emitter 20 and a radiation detector 21 that rotate relative to the subject within angular range 10. When emitter 20 and detector 21 cannot sample all of angular range 10, the angle acquisition range 30 becomes less than the complete angular range 10. FIG. 3 illustrates the angular range 10, including the acquisition range 30 and an unsampled angular range 50. In FIG. 3, there is a single 18 degree gap over the 180 degree range.

The inventors recognized that the missing data that is attributable to a gap of this type could introduce artifacts into reconstructed images.

Figure 4A:
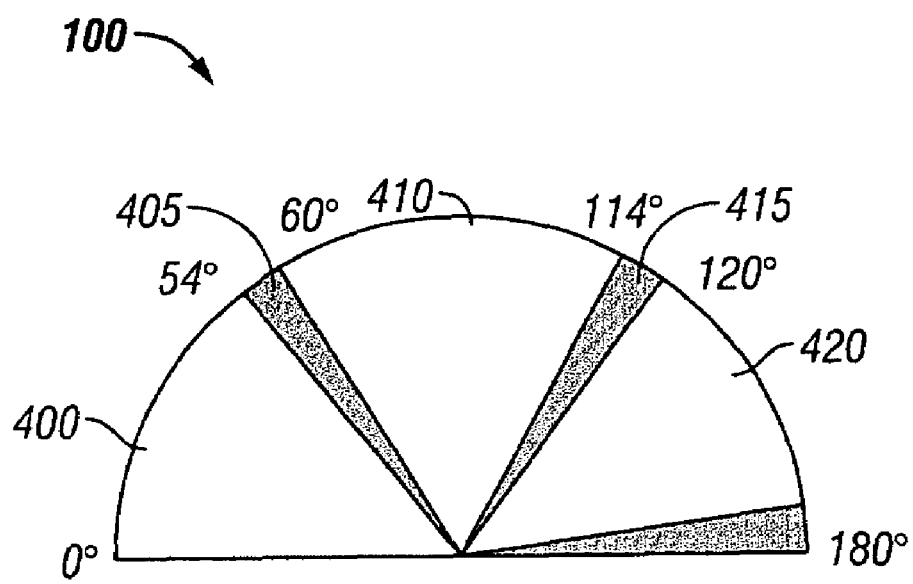
FIG. 4a illustrates an implementation of a computed tomography system with angularly discrete acquisition ranges.

FIG. 4a illustrates a system that is used in an embodiment to obviate this problem. FIG. 4a shows a system that obtains images using angular discrete acquisition. According to FIG. 4a, the 180° arc over which the data is sampled, still has a total of 18° of angular range that is unsampled. This angular range is divided into plural, spaced, unsampled image areas. For example, in FIG. 4a, the overall scan 100 is divided into three obtained areas 400, 410, 420, and three unsampled areas; with unsampled area 405 being between 400 and 410, and unsampled area 415 being between sampled areas 410 and 420.

Figure 4B:
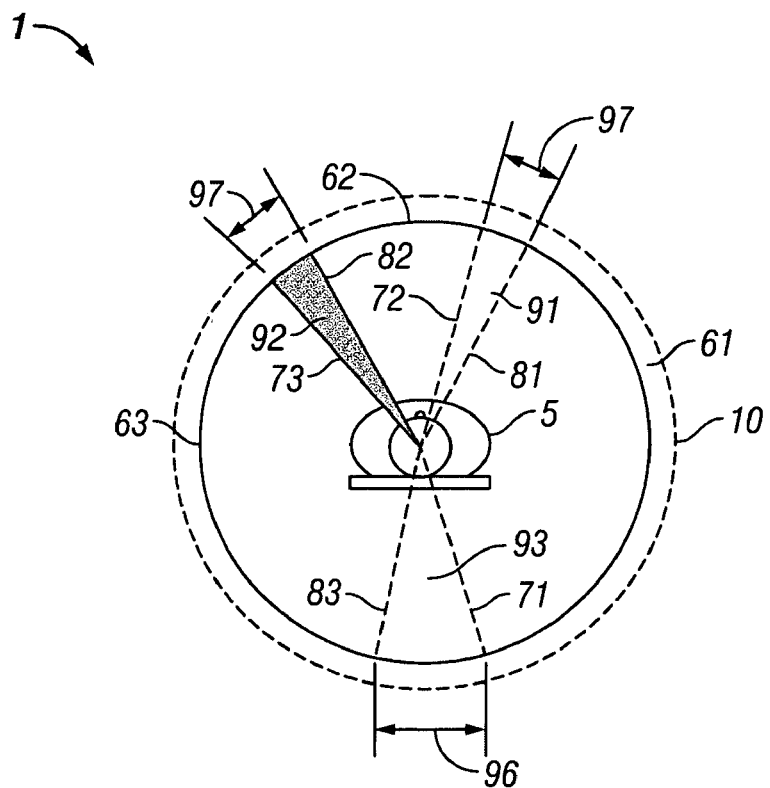
FIG. 4b illustrates an implementation of a computed tomography system with unsampled angular ranges that are unequal in size.

The embodiment of FIG. 4a has a system that is entirely symmetrical, but as described herein, asymmetrical embodiments are also possible. Note that neither discrete continuous acquisition ranges nor unsampled angular ranges 91, 92, 93 need to be of the same size. FIG. 4B illustrates an embodiment where unsampled angular ranges 91, 92, 93 are of different sizes.

In practice, requiring a single continuous acquisition 30 over the entire angular range of interest 10 often puts strong constraints on a computed tomography system 1. The requirement may prohibit integration of features that are practical but may limit the rotation of emitter 20 and detector 21.

In accordance with sampling theory, the angularly discrete acquisition may obtain a complete sampling of subject 5 up to an angular frequency that is determined by the spacing of unsampled angular ranges 91, 92, 93. For example, the angularly discrete acquisition in FIG. 4 is equivalent to two acquisitions. The first acquisition has a low angular frequency, and equivalent to the complete and continuous sampling in the 180° arc with 30 projection views, 6° per projection. The second equivalent acquisition is of a higher angular frequency forming a complementary acquisition in pieces. The first equivalent acquisition allows for an artifact free image reconstruction up to the angular frequency determined by the angular step. The second equivalent acquisition allows obtaining more high-frequency information from the object.

The angular discrete acquisition technique according to the present system may be set according to the desired kind and amount of information. For example, if computed tomography system 1 will not function properly when detector 21 rotates less than a minimal angular frequency, then the largest unsampled angular range 96 should not be greater than the angular step size corresponding to the minimal angular frequency. An alternative embodiment allows the detector to rotate continuously but the acquired data is rebinned as if a certain angular step size is use.

Dividing unsampled-angular range 50 into multiple unsampled angular ranges 61, 62, 63 decreases the size of each unsampled angular ranges 61, 62, 63 and allows for the sampling of higher angular frequencies. Adding detector heads 20 may increase the number of unsampled angular ranges 61, 62, 63. Consequently, a computed tomography system with more detector heads 20 distributed within a given acquisition angular range is advantageous over a system with fewer detector heads.

Figure 5:
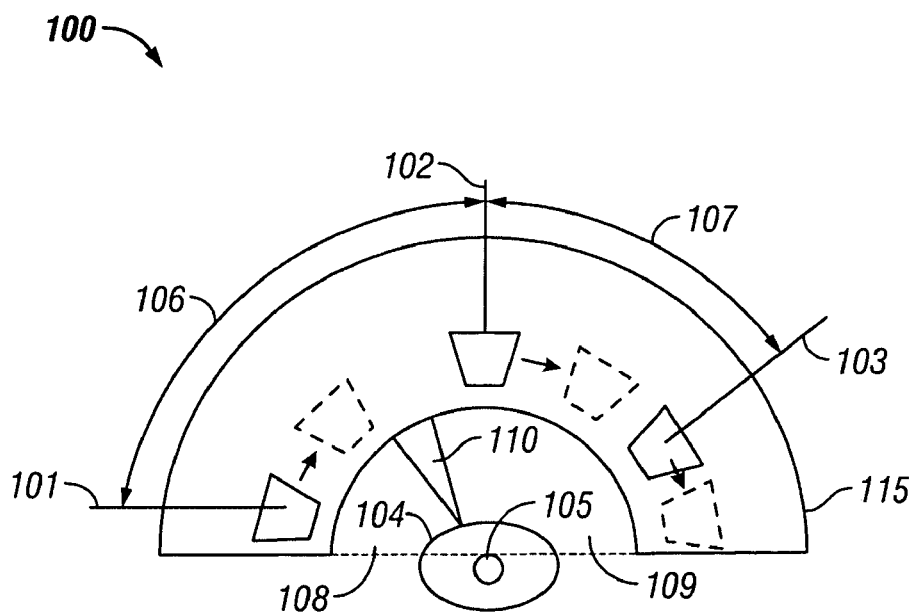
FIG. 5 illustrates an implementation of a computed tomography system having unequally spaced detector heads.

FIG. 5 illustrates a computed tomography system 100 having multiple detector heads 101, 102, 103. The relative rotation of a radiation emitter 105 and radiation detectors 101, 102, 103 is limited by the unequal angular spacing 106, 107 of detector heads 101, 102, 103. Consequently, this system has discrete continuous acquisition ranges 108, 109 separated by unsampled angular range 110. Note that this embodiment might not permit a continuous scan of angular range 115 in conventional systems.

Figure 6:
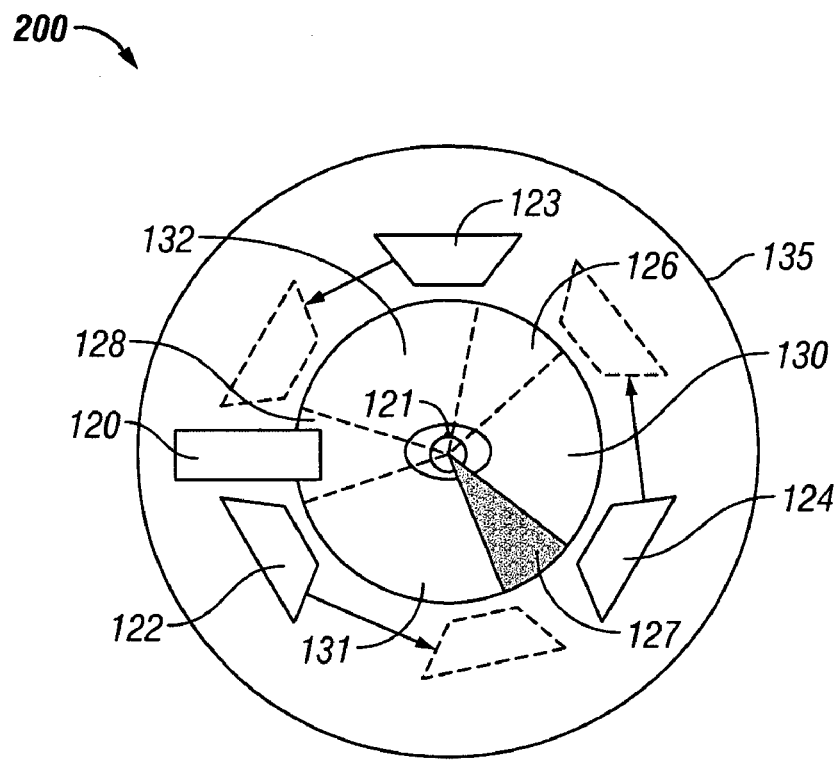
FIG. 6 illustrates an implementation of a computed tomography system having a practical feature that limits the relative rotation of the radiation emitter and the radiation detectors.

FIG. 6 illustrates a computed tomography system 200 having a practical feature, such as a patient support, motion tracking device or motion corrector, that limits the relative rotation of a radiation emitter 121 and several radiation detectors 122, 123, 124. Consequently, this system has discrete continuous acquisition ranges 126, 127, 128 separated by unsampled angular regions 130, 131, 132. This embodiment might not permit a continuous scan of angular range 135 in conventional systems.

Figure 7:
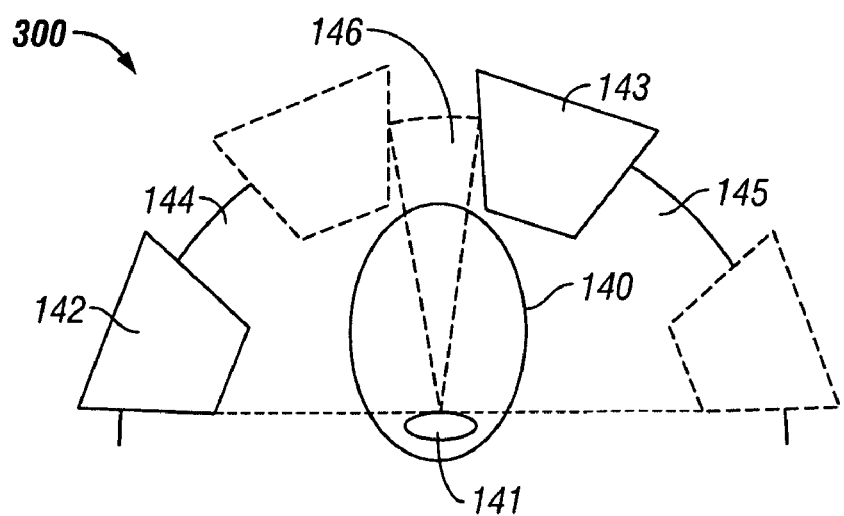
FIG. 7 illustrates an implementation of the computed tomography system wherein the size of the subject to be studied limits the relative rotation of the radiation emitter and the radiation detectors.

FIG. 7 illustrates a computed tomography system 300, wherein the subject 140 limits the relative rotation of a radiation emitter 141 and multiple radiation detectors 142, 143. Consequently, this system has discrete continuous acquisition ranges 144, 145 separated by an unsampled angular region 146.

In carrying out the angularly discrete acquisition technique in the above mentioned computed tomography systems, the computed tomography system samples a first discrete continuous acquisition range and a second discrete continuous acquisition range. In systems with one radiation detector and one radiation emitter, the emitter and the detector rotate with respect to each other throughout the unsampled angular range(s) but do not collect any data. Consequently, the discrete continuous acquisition ranges are sampled consecutively.

In computed tomography systems with multiple detector heads and/or emitters, the system may either rotate through the unsampled angular ranges or not. In either case, the discrete continuous acquisition ranges are sampled simultaneously. For example, FIG. 6 illustrates a three-head 122, 123, 124 computed tomography system 200 that is rotationally limited. Thus detector heads 122, 123, 124 do not rotate relative to radiation emitter 121 through unsampled angular ranges 126, 127, 128, and discrete continuous acquisition ranges 130, 131, 132 are sampled simultaneously.

Figure 8:
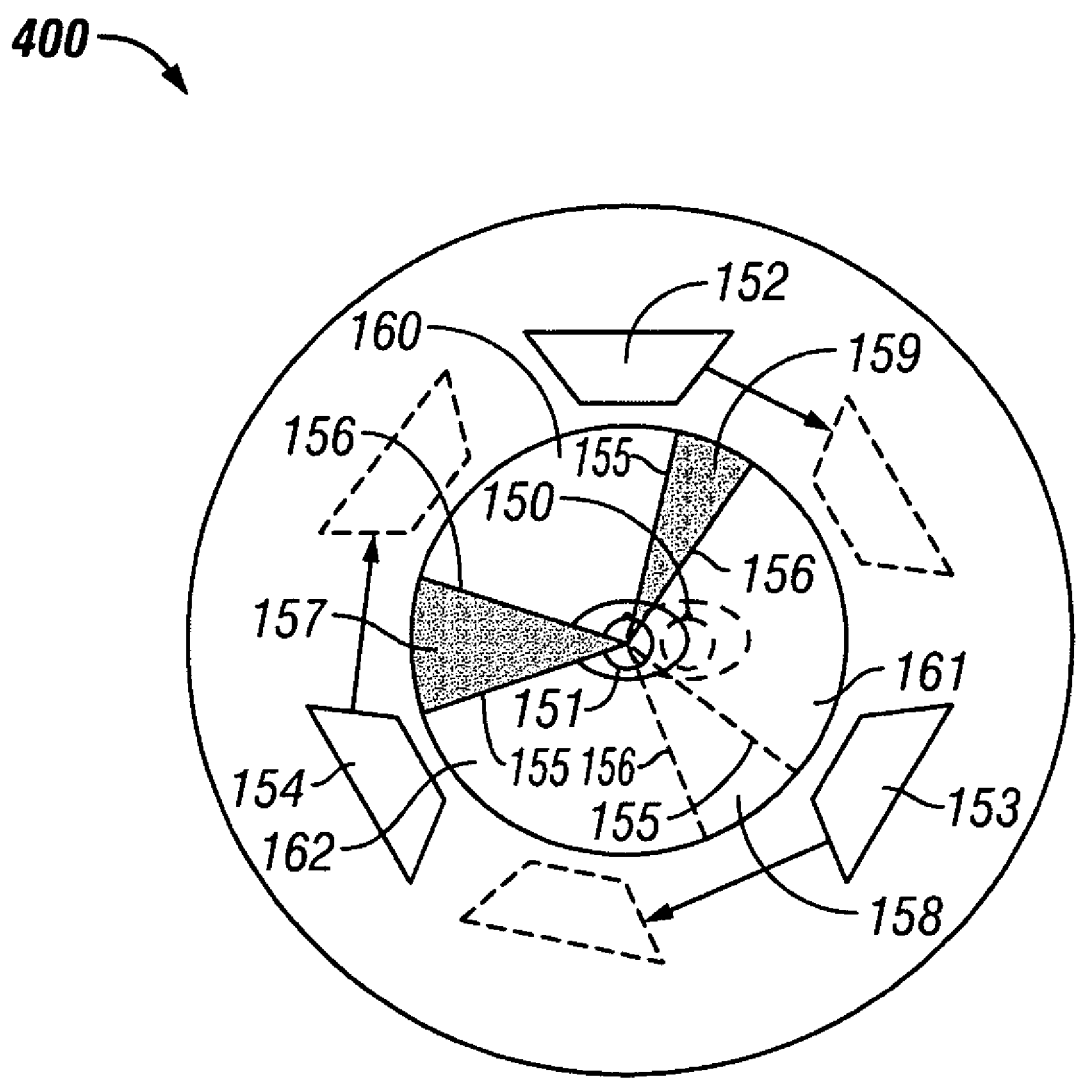
FIG. 8 illustrates an implementation of a computed tomography system wherein the subject to be studied moves substantially while the radiation emitter and the radiation detectors are rotating with respect to each other.

FIG. 8 illustrates a computed tomography system 400, wherein the subject 150 moves significantly when a radiation emitter 151 and multiple radiation detectors 152, 153, 154 have rotated to a first angle 155 that marks the beginning of the movement. When radiation emitter 151 and radiation detector 152 have rotated to a second angle 156, subject 150 returns to the position it occupied prior to detectors 152, 153, 154 reaching angle 155. First angles 155 and second angles 156 bound discardable angular ranges 157, 158, 159 that can be excluded to create discrete continuous acquisition ranges 160, 161, 162. Thus, although computed tomography system 300 is not rotationally limited, the data acquired is equivalent to that of computed tomography system 200 in FIG. 6.

Note that the angularly discrete acquisition technique discussed above may also be controlled by a computer.

The general structure and techniques, and more specific embodiments which can be used to affect different ways of carrying out the more general goals are described herein.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, those skilled in the operation and design of medical imaging systems, e.g. computed tomography systems.

Also, the inventors intend that only those claims which use the words "means for" are intended to be interpreted under 35 U.S.C. §112¶6. Moreover, no limitations from the specification are intended to be read into any claims, unless those limitations are expressly included in the claims. The computers described herein may be any kind of computer, either general purpose, or some specific purpose computer such as a workstation. The computer may be a Pentium class computer, running Windows XP or Linux, or may be a Macintosh computer. The computer may also be a handheld computer, such as a PDA, cell phone, or laptop.

The programs may be written in C, or Java, Brew or any other programming language. The programs may be resident on a storage medium, e.g. magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

What is claimed is:

1. A medical imaging system comprising:
    a radiation detector configured to scan an object;
    a rotating part that rotates at least one of said radiation detector and the object with respect to each over an angular range,
    a controlling part for the detector, controlling the detector for scanning over a first discrete continuous acquisition range having a first start angle and a first end angle, and a second discrete continuous acquisition range having a second start angle and a second end angle, and a third discrete continuous acquisition range having a third start angle and a third end angle, wherein the first end angle and the second start angle are separated by a first unsampled angular range, and wherein the second end angle and the third start angle are separated by a second unsampled angular range, which is separated from the first unsampled angular range, wherein said controlling part controls the scan such that there is not a complete scan, and there is no scanning between said first and second continuous acquisition range, and there is no scanning between said second and third continuous acquisition ranges, wherein the medical imaging system is a computed tomography system that uses data from each of said first discrete continuous acquisition range, and said second discrete continuous acquisition range, and said third discrete continuous acquisition range, to form a medical image and where said medical image is formed without using data in between said first and second continuous acquisition range, and wherein said data part forms said image without using data in between said second and third continuous acquisition ranges, to form said medical image.

2. The medical imaging system of claim 1 wherein the rotating part rotates at an angular step size that is greater than the minimum angular step size of the computed tomography system.

3. The medical imaging system of claim 1 wherein the radiation detector comprises a plurality of separated radiation detectors, wherein the plurality of separated radiation detectors are relatively rotatable with respect to the object.

4. The medical imaging system of claim 1, wherein the first unsampled angular range is larger than said second unsampled angular range.

5. The medical imaging system of claim 4, wherein the first unsampled angular range is not smaller than a minimum angular step size of the medical imaging system.

6. The medical imaging system of claim 1 further comprising a part that limits the relative rotation of the radiation detector and the radiation emitter.

7. The medical imaging system of claim 6, wherein the part is selected from the group consisting of motion tracking devices, patient supports and motion correctors.

8. The medical imaging system of claim 1 further comprising a data processing system arranged to acquire discontinuous sampling data and uses data from each of said first discrete continuous acquisition range, and said second discrete continuous acquisition range to form a medical image.

9. The medical imaging system of claim 1 wherein the medical imaging system is selected from the group consisting of computed axial tomography, single photon emission medical imaging, and positron emission tomography that uses data from each of said first discrete continuous acquisition range, and said second discrete continuous acquisition range, and said third discrete continuous acquisition range, to form a medical image.

10. A method of angularly discrete data acquisition for medical imaging comprising:
    scanning over a first discrete continuous acquisition range within an overall angular range;
    scanning over a second discrete continuous acquisition range within the overall angular range;
    scanning over a third discrete continuous acquisition range within the overall angular range;
    wherein the first discrete continuous acquisition range and the second discrete continuous acquisition range are separated by a first unsampled angular range, and the second and third discrete continuous acquisition ranges are separated by a second unsampled angular range;
    not obtaining scanning data over said unsampled angular ranges, wherein the scan is controlled such that there is not a complete scan, and there is no scanning between said first and second continuous acquisition range, and there is no scanning between said second and third continuous acquisition ranges.

11. The method of discrete data acquisition for medical imaging of claim 10 further comprising decreasing a size of the unsampled angular range to enable sampling of higher angular frequencies.

12. The method of discrete data acquisition for medical imaging of claim 10 further comprising increasing a number of unsampled angular ranges.

13. The method of discrete data acquisition for medical imaging of claim 10 further comprising excluding a discardable angular range, wherein the discardable angular range is bound by a first angle and a second angle, wherein a subject to be studied moves from a first position to a second position at the first angle and returns to the first position at the second angle.

14. A method as in claim 10, further comprising using data from each of said first discrete continuous acquisition range, and said second discrete continuous acquisition range, and said third discrete continuous acquisition range, to form a medical image.

15. A computer-readable storage medium containing a set of instructions for a general purpose computer having a user interface comprising a mouse and a screen display, which, when executed, cause actions comprising:

measuring a first discrete continuous acquisition range within an angular range;

measuring a second discrete continuous acquisition range within the angular range, wherein the first discrete continuous acquisition range and the second discrete continuous acquisition range are separated by a second unsampled angular range;

measuring a third discrete continuous acquisition range within the angular range, wherein the second discrete continuous acquisition range and the third discrete continuous acquisition range are separated by a second unsampled angular range; and not measuring within the unsampled angular ranges;

controlling the acquisition range such that there is not a complete scan, and there is no scanning between said first and second continuous acquisition range, and there is no scanning between said second and third continuous acquisition ranges.

16. The data storage device of claim 15 further comprising increasing a number of unsampled angular ranges, thereby decreasing the size of each unsampled angular ranges, whereby the sampling of higher angular frequencies is enabled.

17. The method of discrete data acquisition for medical imaging of claim 15 further comprising excluding a discardable angular range, wherein the discardable angular range is bound by a first angle and a second angle, wherein a subject to be studied moves from a first position to a second position at the first angle and returns to the first position at the second angle.

18. A medical imaging system comprising a data processing system arranged to:

sample a first discrete continuous acquisition range having a first starting angle and a first ending angle, wherein the first discrete continuous acquisition range is a subset of an angular range; and sample a second discrete continuous acquisition range having a second starting angle and a second ending angle, wherein the second discrete continuous acquisition range is a subset of the angular range, and the first discrete continuous acquisition range and the second discrete continuous acquisition range are separated by an unsampled angular range, sample a second discrete continuous acquisition range having a second starting angle and a second ending angle, wherein the second discrete continuous acquisition range is a subset of the angular range and the first discrete continuous acquisition range and the second discrete continuous acquisition range are separated by an unsampled angular range, wherein the unsampled angular range is a subset of the angular range;

control the sampling such that there is not a complete scan, and there is no scanning between said first and second continuous acquisition range, and there is no scanning between said second and third continuous acquisition ranges, form a medical image using data from each of said first discrete continuous acquisition range, and said second discrete continuous acquisition range, and said third discrete continuous acquisition range, without using data in between said first and second continuous acquisition range, and without using data in between said second and third continuous acquisition ranges to form said medical image.

* * * * *